United States Patent [19]
Qureshi et al.

[11] Patent Number: 5,951,587
[45] Date of Patent: Sep. 14, 1999

[54] NEEDLE HOLDER WITH SUTURE FILAMENT GRASPING ABILITIES

[75] Inventors: Saleem U. Qureshi, West Chester; Kip M. Rupp, New Richmond; Bennie Thompson, Cincinnati, all of Ohio

[73] Assignee: Ethicon-Endo-Surgery, Inc., Cincinnati, Ohio

[21] Appl. No.: 08/948,159

[22] Filed: Oct. 9, 1997

[51] Int. Cl.$^6$ .................................................. A61B 17/28
[52] U.S. Cl. ........................... 606/207; 606/144; 606/147
[58] Field of Search ..................................... 606/147, 148, 606/207, 206, 205, 139

[56] References Cited

U.S. PATENT DOCUMENTS

| | | |
|---|---|---|
| 1,445,348 | 2/1923 | Noble . |
| 3,608,554 | 9/1971 | McGuinness ............................ 606/207 |
| 5,304,185 | 4/1994 | Taylor . |
| 5,413,583 | 5/1995 | Wohlers . |
| 5,601,575 | 2/1997 | Measamer et al. . |

Primary Examiner—Michael Buiz
Assistant Examiner—Julian W. Woo
Attorney, Agent, or Firm—Matthew S. Goodwin

[57] ABSTRACT

A surgical needle holder for use in open or laparoscopic surgery, that grasps a needle or a suture filament. The needle holder has a lower jaw, and an upper jaw moveable from an open to a closed position. The lower jaw has a pair of lower jaw ledge surfaces and a groove. The upper jaw has a grasping protrusion surface that can be embedded within a groove in the lower jaw, when the upper jaw is closed. When the jaws are closed on a needle, it is grasped with a three point needle contact system. The needle contact points are the two lower jaw ledges and the upper jaw grasping protrusion surface. Closure of the jaws on a curved needle "rights" the needle. When the jaws are closed on a suture filament, the upper jaw protrusion surface and the groove form a labyrinth path that effectively grasps the suture filament relative to the end effector. This enables the surgeon to apply tension to a suture to produce a tight knot or, when proximating tissue, tension a suture loop.

6 Claims, 6 Drawing Sheets

NEEDLE HOLDER WITH SUTURE FILAMENT GRASPING ABILITIES

BACKGROUND

The present invention relates in general to needle holders for use in surgery, and in particular, to endoscopic needle holders with suture grasping abilities.

In endoscopic surgery, one or more needle holders are used with specialized surgical needles (wherein the needle is swaged or attached to the suture), to apply a suture to a surgical site within a patients body. Needle holders can be used in conjunction with other surgical devices such as knot deploying devices, knot tying devices, and needle driving devices. The needle holder is introduced through a cannula and is manipulated by the operator. The needle holder is generally comprised of a handle, an elongated shaft and a pair of grasping jaws. One or more jaws are moveable and are actuated by manipulation of handle controls. The jaws grasp the surgical needle and are used to manipulate the needle to produce endoscopic sutures.

Needle holders can hold or grasp various sized surgical needles at any position, proximal or distal, within the grasper jaws. For a given force input at the handle, the force exerted upon the needle by the jaw components varies as a function of the distance of the needle from the moveable jaw pivot point, and the needle diameter. The more distal the needle grasping location, the higher the forces on the needle, the bearings, and the clamping jaw. The larger the needle diameter, the higher the forces on the needle and jaw components. Thus, grasping a large diameter needle within the distal portion of the jaws could damage both the needle and instrument, or reduce the life of the instrument. It would therefore be desirable to apply a force limiting device within the needle holder to limit the amount of force applied by the grasper jaws, regardless of the position of the closure trigger, or needle diameter. Such a device is described in U.S. Pat. No. 5,413, 583 by Udo Wohlers, herein incorporated as a reference.

With the addition of a force limiting device to the needle holder, endoscopic suturing became easier and more readily accepted. However, there were still difficulties in grasping and manipulating needles in the laparoscopic environment. Control of the needle is important for endoscopic suture placement. Three distinct types of needle motion within the grasper jaws are possible, these are: 1.) needle rotation, wherein the needle point and swage rotate in unison about the grasping point; 2.) needle toggling, wherein the point and swage move, in the same plane, and in opposite directions about the grasping point; 3.) needle slippage, wherein the needle slides within the jaws and the grasping point moves closer to the tip of the needle. Additionally, it is of great value to position the needle into the needle holder in a generally transverse orientation that is suitable for placing a stitch. As described by Measamer et al. in U.S. Pat. No. 5,601,575 herein incorporated as a reference, the use of a three point needle system grasping system in conjunction with a curved needle addressed these issues. Additionally, the three point grasper design described causes the needle to "right" or snap into a position wherein the needle curvature is vertical and perpendicular to the longitudinal axis of the instrument. The "righted" needle position greatly facilitates the needle placement, but is not adequate to grasp suture.

With the breakthrough "righting" needle feature, endoscopic suturing reached a new level. However, there are still difficulties with endoscopic suturing as the needle grasper can only grasp the needle, and is not adequate to grasp suture. In endoscopic surgery, the space available within the patient is limited. Additionally, the surgical site is crowded with surgical devices such as trocar cannulas, dissectors, graspers, knot tying devices, and the like. The restricted space, when combined with a long suture, and the limited range of motion available with endoscopic access ports, can make it very difficult to tighten a stitch or knot. Thus it would be advantageous, when tying a knot or tensioning a suture loop, to grasp the suture close to the stitch or knot, rather than at the needle in connection with use of an instrument that grasps a needle.

SUMMARY OF THE INVENTION

Accordingly, the present invention is a surgical needle holder for grasping a surgical needle or a suture filament. The needle holder is comprised of a lower and an upper jaw.

The lower jaw having a pair of spaced apart lower jaw ledges, each of which has a lower jaw ledge surface. A pair of spaced apart lower floor surfaces are adjacent to the ledge surfaces. A groove is interposed between and descending from the lower floor surfaces.

The upper jaw is facing the lower jaw and has a grasping protrusion surface. The grasping protrusion surface extending downwardly from the upper jaw. The upper jaw is moveable from an open position, spaced from the lower jaw, to a closed position adjacent to the lower jaw. When the upper jaw is in the closed position, the grasping protrusion surface is embedded within and contacts the groove.

When the needle is positioned between the open lower and upper jaws, and the upper jaw is closed, the needle is grasped between the grasping protrusion surface and the lower jaw ledge surfaces.

When the suture filament is positioned between the open lower and upper jaws, and the upper jaw is closed, the suture filament is secured between the groove and the grasping protrusion surface embedded in the groove.

Significantly, the combination of a surgical needle holder with suture grasping abilities offers many advantages. The suture grasping ability enables the surgeon to grasp the suture close to the knot or stitch. Since suture stretches some linear amount per unit of length, reducing the suture length between the stitch site and the needle grasper effectively reduces the amount of suture stretch. This produces a tighter knot or stitch as more of the tensioning energy is used to tie the knot, not stretch a long suture.

Additionally, in endoscopic surgery internal space within the patient is at a premium. Using a needle driver that grasps only a needle is difficult when combined with a long suture, a confined space, and the limited range of motion from the access port. Using a needle holder that grasps the suture near the stitch or knot lessens the procedural difficulty and is a great advantage.

Another advantage of this invention is its ability to be used in conjunction with other instruments such as other needle holders, knot deployment devices, or knot tying devices. The ability to grasp the needle, or suture, or tissue will enhance the usage of these devices.

In short, the surgical needle holder of the present invention provides significant advantages to endoscopic suturing. The enhanced ability of this device to grasp surgical needles, tissue, and suture, reduces the difficulties of endoscopic suturing. Additionally, the device can be used to enhance surgical procedures in conjunction with knot tying or deployment instruments.

DETAILED DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
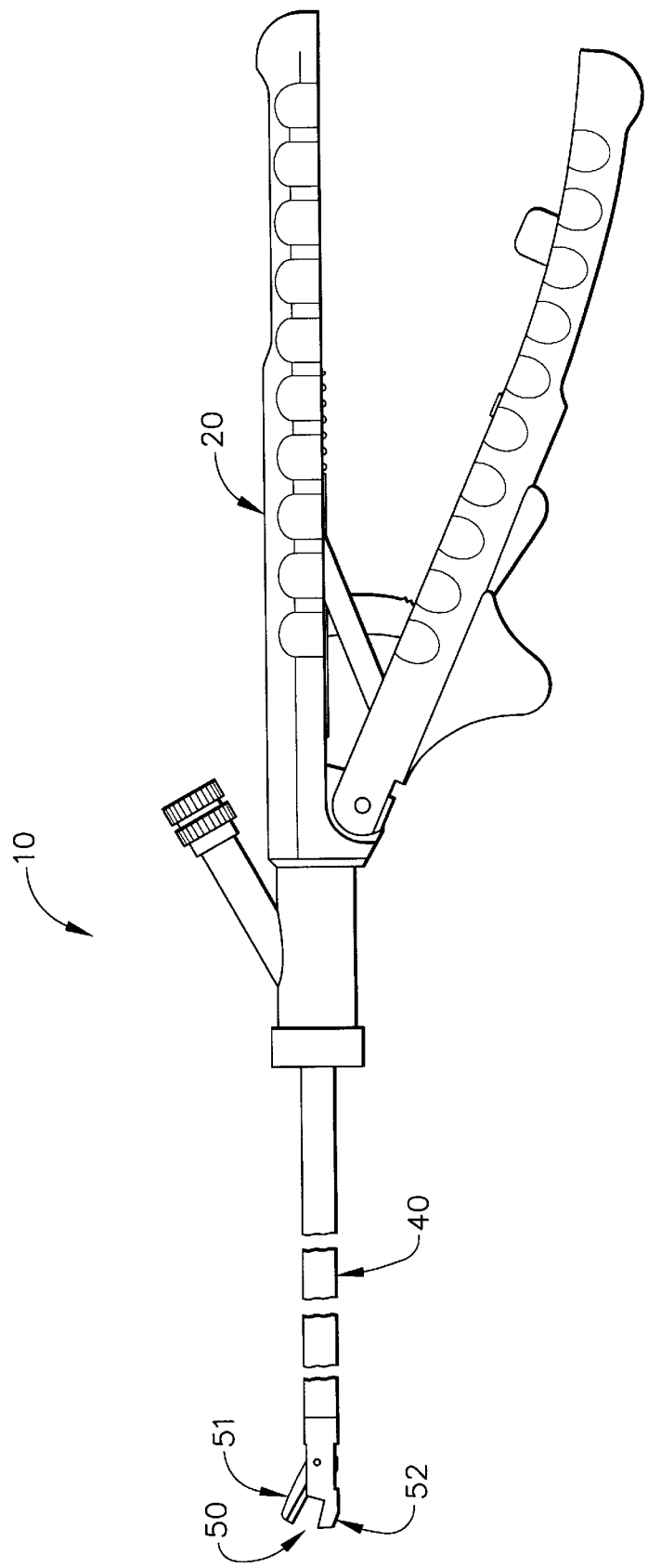
FIG. 1 is a side view of a surgical needle holding instrument of the present invention.

As best shown in FIG. 1, the present invention is a surgical needle holder 10, utilized for endoscopic or open surgical procedures. The needle holder 10 comprises a proximal handle 20, an elongated shaft 40, and a distal end effector 50. The distal end of the device 10 is comprised of a fixed lower jaw 52 and a moveable upper jaw 51. The upper jaw 51 of the end effector 50, is moveable from a first open position to a second position to effectively grasp a needle, tissue, or surgical suture. The elongated shaft 40 and end effector 50 are insertable through a cannula for endoscopic surgery.

Figure 2:
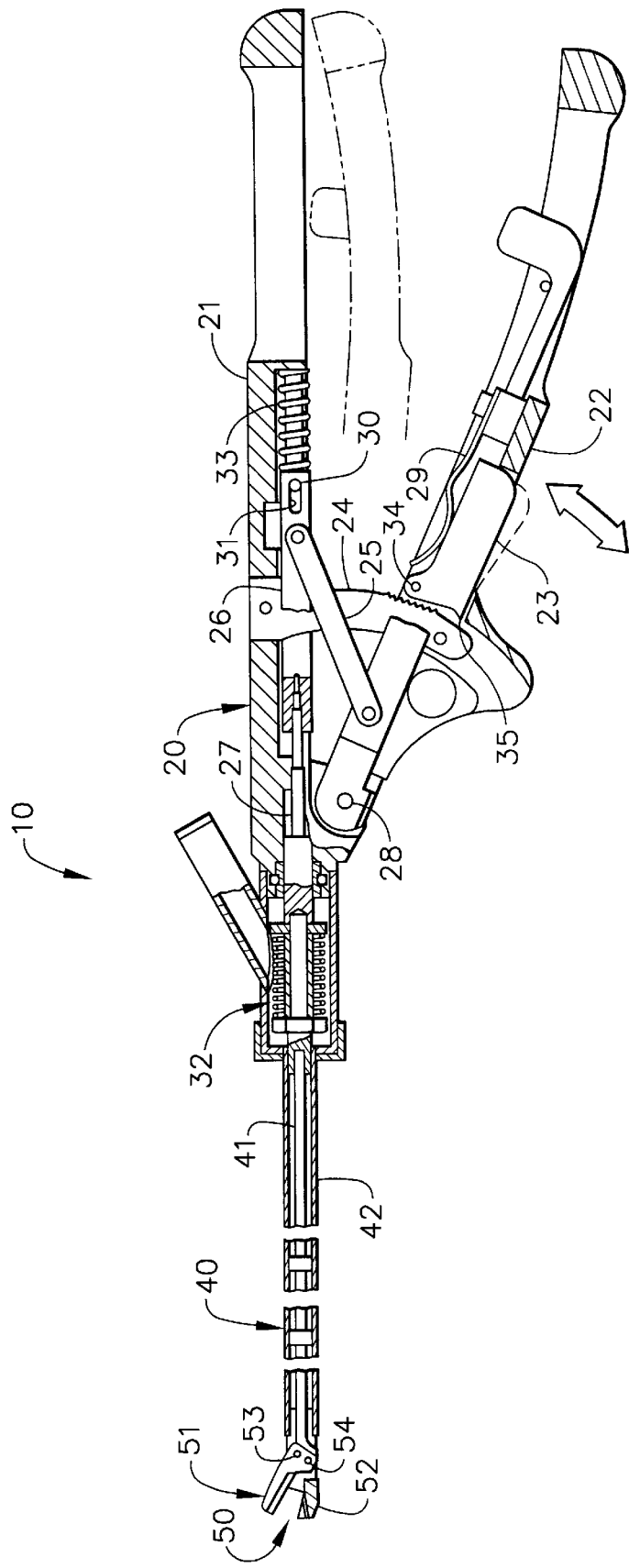
FIG. 2 is the side view of FIG. 1, wherein the instrument has been sectioned for a view of the internal components.

Referring now to the instrument cross section as shown in FIG. 2, with the exception of the distal end effector 50, the instrument is generally disclosed in the Wohlers U.S. Pat. No. 5,413,583, which is incorporated by reference. As described in this patent, the shape of the handle or grip arrangement can vary and still meet design intent.

The handle consists of a body 21 and a generally rectangular elongate trigger 22. The handle trigger 22 is pivotally mounted to the handle body 21, about handle pin 28. Closure of the handle trigger 22, towards the handle body 21, results in proximal motion of the handle block 26, compression of the return spring 33, closure of the jaws at the distal end of the instrument, and engagement of a one way ratchet mechanism. Trigger release pawl 24 is shown in engaged position.

The ratchet mechanism subassembly holds the jaws firmly closed to constrain the needle. The ratchet mechanism is comprised of trigger release pawl 23, ratchet plate 24, pawl pivot pin 34, and pawl spring 29. Depression of the trigger release pawl 23 inwardly see (FIG. 2) releases the pawl tooth 35, located on the trigger release pawl 23, from the ratchet plate 24 and the return spring 33 biases the trigger 23 and jaws open, releasing the needle 70 or suture filament 72.

Handle trigger 22 is coupled to the generally rectangular elongate handle block 26 by one or more trigger links 25. Inward movement of the trigger 23 is transmitted by trigger links 25 and results in proximal longitudinal motion of the handle block 26 and compression of the return spring 33. The handle block 26 is moveably coupled, in the longitudinal direction, to the handle body 21, by block pin 30 in block slot 31. The handle block 26 is fixably coupled to the proximal shaft 27. Proximal shaft 27 is coupled to the proximal end of actuation shaft 41 by a force limiting coupling 32 as described in the Wohlers patent listed above. This coupling limits the amount of force that can be applied by the upper jaw 51 In the Wohlers device, a series of compressible springs are used as the force limiting device.

The actuation shaft 41 is slideably and concentrically mounted within the bore running longitudinally in the exterior shaft 42. The proximal end of the exterior shaft 42, is fixably mounted to the distal end of the handle 20. The distal end of the exterior shaft 42 is fixably mounted to the proximal end of the lower jaw 51.

As shown in FIGS. 1 through 6, the lower jaw 52 is generally cylindrical in shape with a channel running longitudinally within. A generally "L" shaped upper jaw 51 (see FIG. 2) is pivotally mounted within upper slot 55 of the lower jaw 52, about jaw pivot pin 53 (see FIG. 3). The lower end of the upper jaw 51 is hingeably connected to the actuation shaft 41 by actuation shaft pin 54 as shown in FIG. 2. Proximal movement of the actuation shaft 41 results in upper jaw 51 pivoting closed about pivot pin 53. A grasping protrusion 63 lies along the longitudinal axis and extends inwardly from a pair of spaced-apart inner surface 65 of the upper jaw 51 (see FIG. 3). Upper jaw grasping protrusion surface 57 is located on the inward side of the grasping protrusion 63. A grasping protrusion 63 lies along the longitudinal axis and extends inwardly from a pair of upper floor surfaces 51 (see FIG. 3). Upper jaw grasping surface 57 is located on the inward side of the grasping blade 53.

A "U" shaped channel 56, extends distally from the proximal end of the lower jaw 52. This channel provides two lower jaw ledge surfaces 58 located on the spaced-apart lower jaw ledges 67. When closed, the upper jaw 51 pivots within the "U" shaped channel 56 and the grasping protrusion surface 57 is embedded in and contacts the groove 61. Clearance is supplied between the inner ledge surfaces 59 and the outer jaw surfaces 60 of the upper jaw 51 (see FIGS. 5 and 6).

Figure 4:
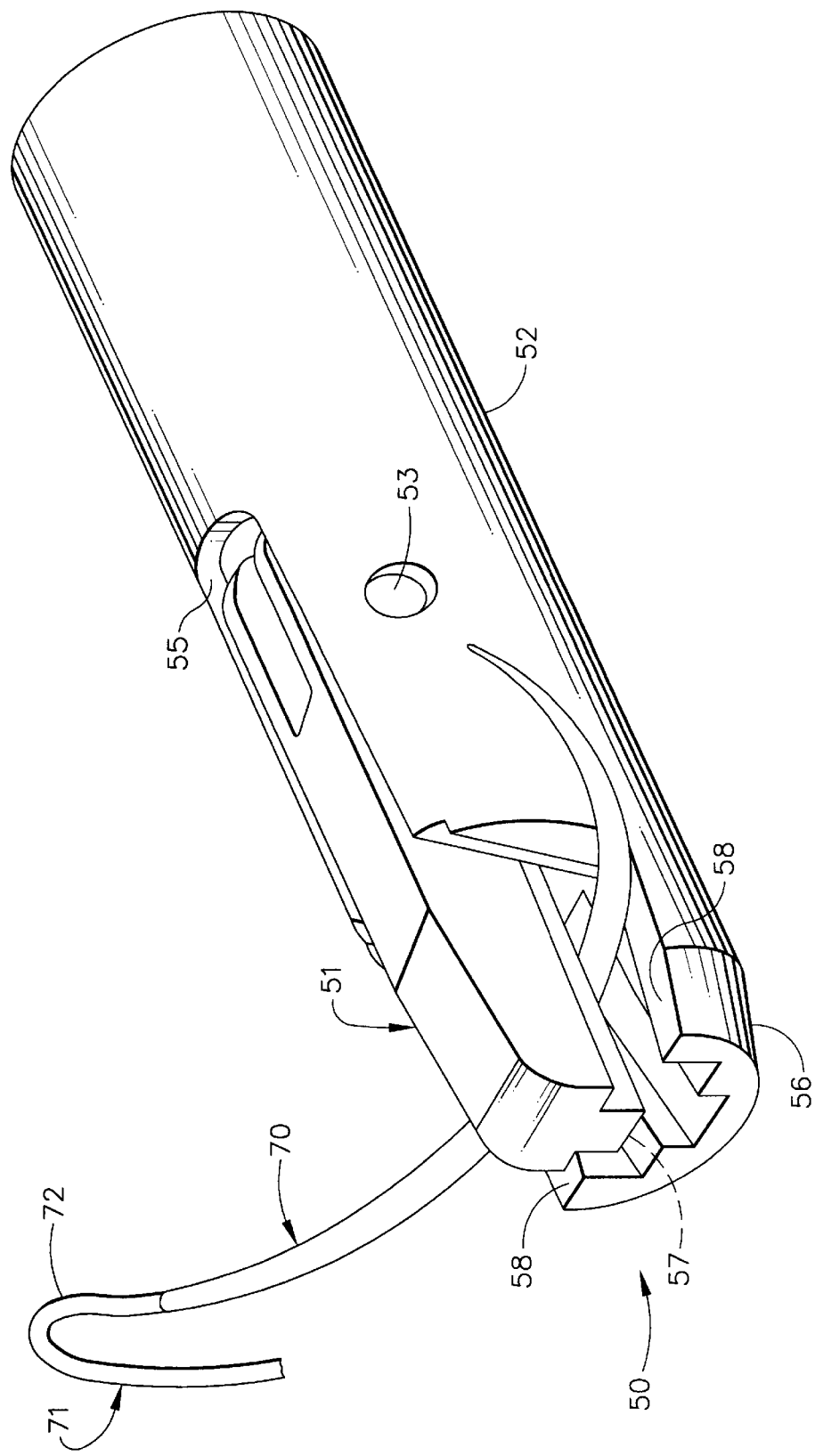
FIG. 4 is the perspective view of FIG. 3 with a surgical needle grasped within the jaws of the end effector.

As shown in FIG. 4, a surgical needle 70 is captured within the distal jaws of the needle holder. The needle 70, is constrained by three discreet contact points comprised of the lower jaw ledge surfaces 58 and the upper jaw grasping protrusion surface 57. As disclosed by Measamer et al. in U.S. Pat. No. 5,601,575, which is herein incorporated for reference, this geometry causes the needle 70 to "right" or snap to a position wherein the plane of the curvature of the needle is vertical and perpendicular to the longitudinal axis of the instrument (see FIG. 4). Thus, the jaws of the present invention incorporate the "self righting" needle feature.

Figure 3:
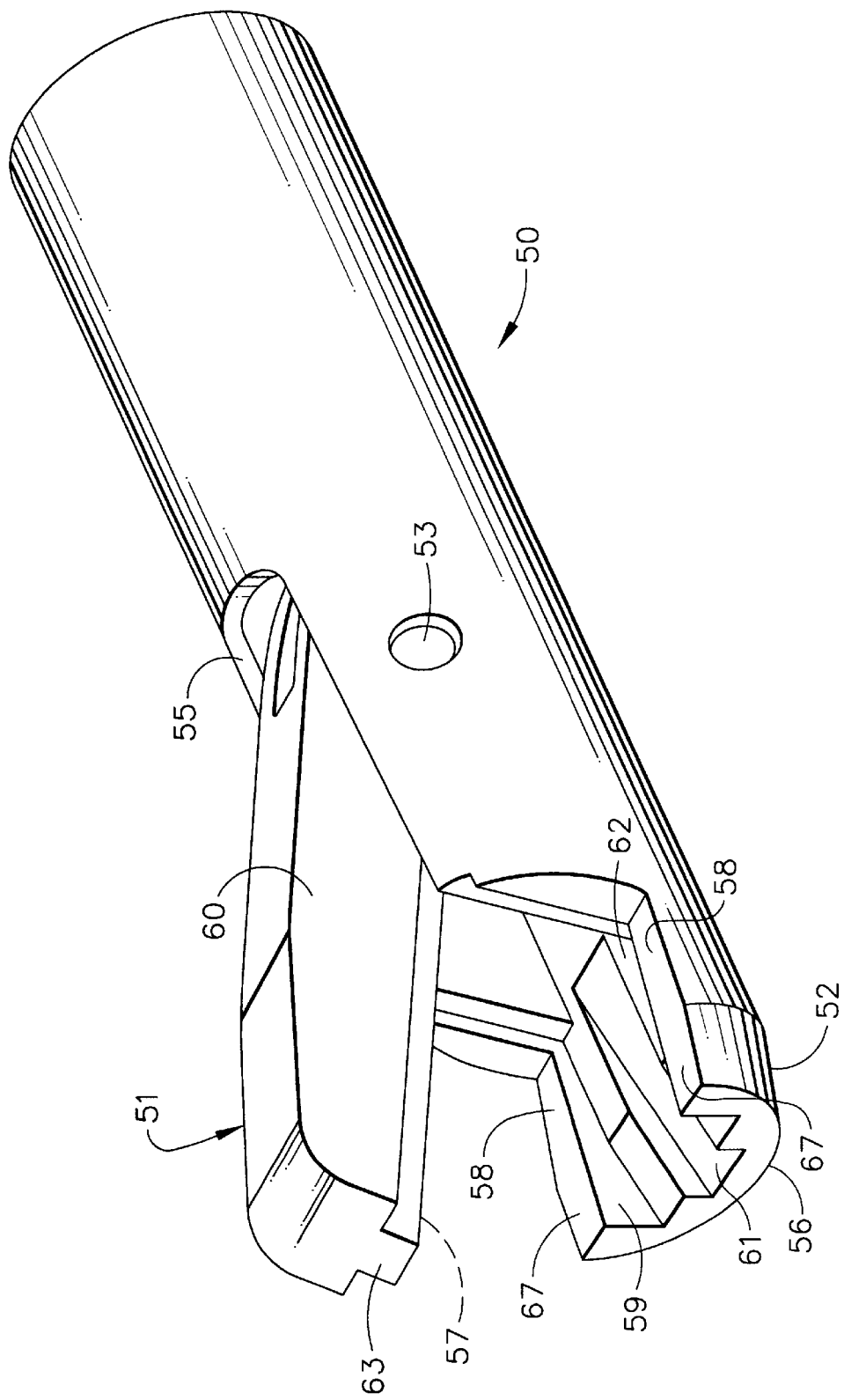
FIG. 3 is a perspective view of an end effector of the instrument with a fixed lower jaw and an open upper jaw.

Referring now to FIG. 3, a groove 61 is located between and descends from the floor surfaces 62 of the "U" channel 56. The groove 61 is angled for parallel closure with upper jaw grasping protrusion surface 57 when the upper jaw 51 is fully closed. When fully closed, with no object within the jaws, the grasping protrusion 63 ,of the upper jaw 51, resides within the groove 61 with the upper jaw grasping protrusion surface 57 in contact with the floor of the inner groove 61.

Figure 5:
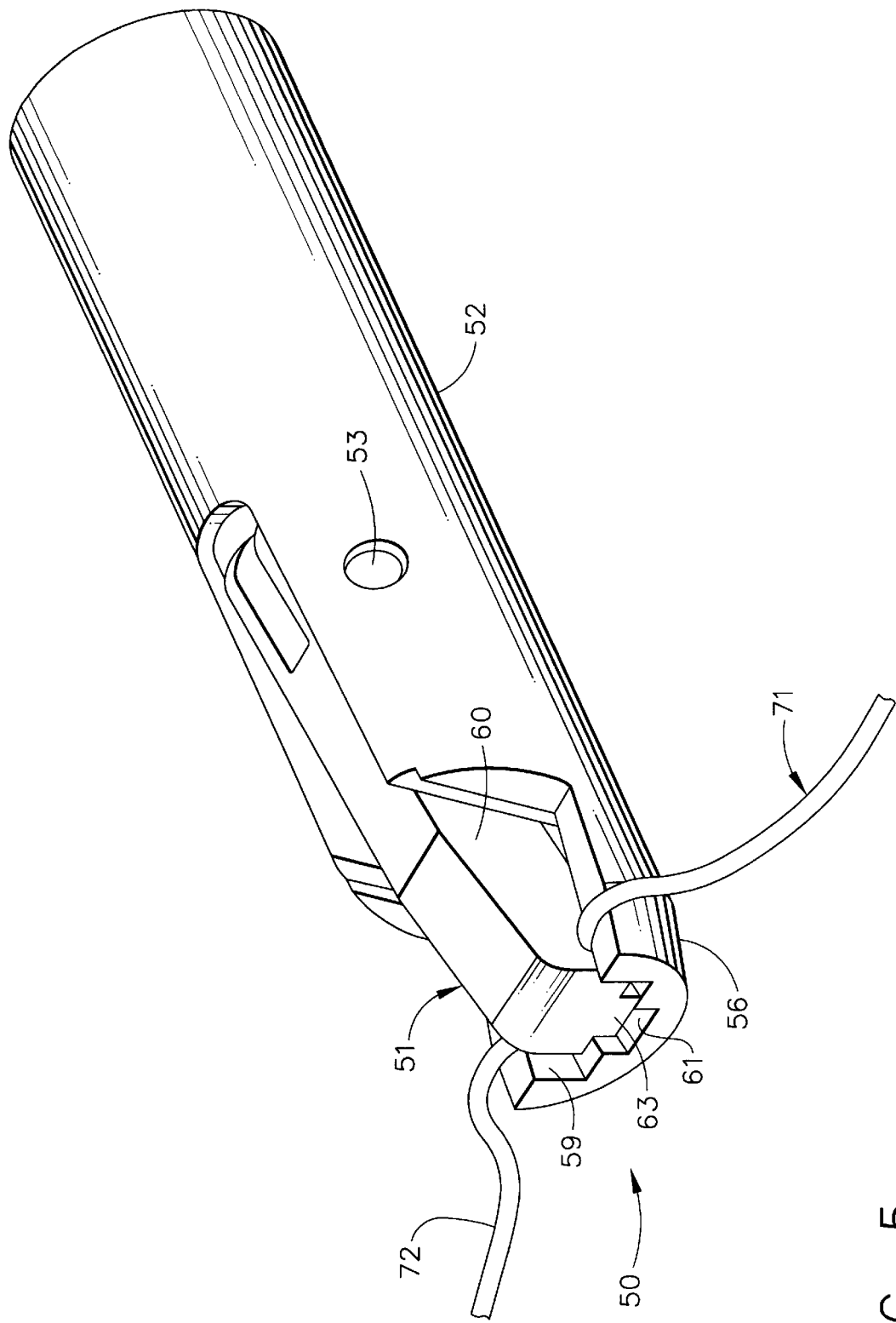
FIG. 5 is the perspective view of FIG. 3 with a suture filament grasped within the jaws of the end effector.
Figure 6:
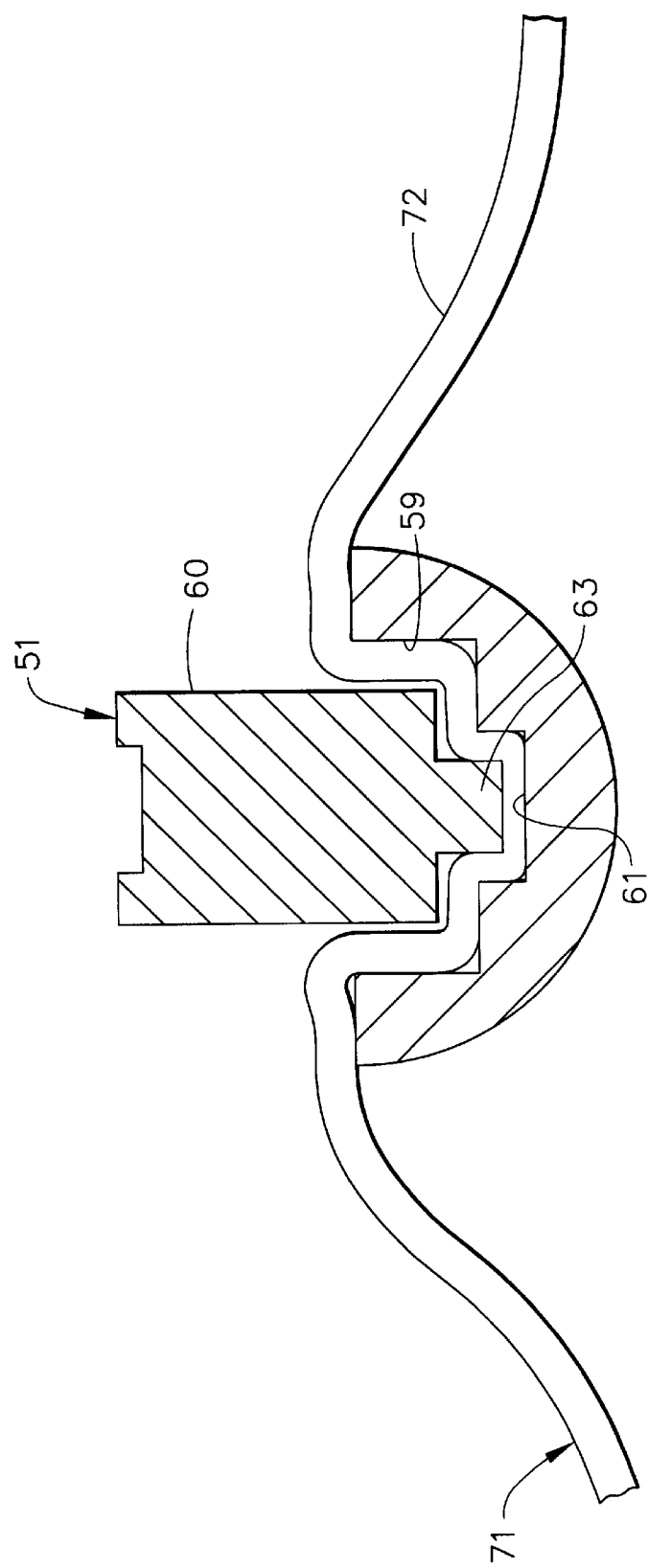
FIG. 6 is a section view of FIG. 5 wherein the suture is firmly grasped within the jaws of the instrument showing the labyrinth path of the suture filament.

As shown in FIGS. 5 and 6, when the upper jaw 51 is closed on suture filament 72, the groove 61, in combination with the grasping protrusion 63 on the upper jaw 51, form a labyrinth path (see FIG. 6.) that effectively grasps the suture filament 72. The labrynth path constrains the suture filament 72 relative to the end effector 50 and enables the surgeon to apply tension to produce a tight knot, or tension a suture loop when proximating tissue. Such a feature is of value in surgery where knot security is of great importance. Additionally, the upper and lower jaws can be used to effectively grasp and manipulate tissue.

Whereas the preferred invention utilizes a labyrinth path design to grasp suture, it should be obvious to one skilled in the art that a variety of paths are available to enable a needle holder to grasp suture.

While preferred embodiments of the present invention have been shown and described herein, it will be obvious to those skilled in the art that such embodiments are provided by way of example only. Numerous variations, changes, and substitutions will now occur to those skilled in the art without departing from the invention. Whereas the invention is described for use during endoscopic surgery, it is apparent that the invention can be used for open or general surgery. Accordingly, it is intended that the invention be limited only by the spirit and scope of the appended claims.

What is claimed is:

1. A surgical needle holder for grasping a surgical needle or a suture filament, said needle holder comprising:
    a lower jaw having:
        i) a pair of spaced-apart lower jaw ledges, each of said ledges having a lower jaw ledge surface thereon,
        ii) a pair of spaced-apart lower floor surfaces adjacent said ledge surfaces, and
        iii) a groove interposed between and descending from said lower floor surfaces, said groove being sloped downwardly from a proximal end of said lower jaw to a distal end of said lower jaw; and
    an upper jaw facing said lower jaw, said upper jaw having a grasping protrusion surface from said upper jaw, said upper jaw moveable from an open position spaced from said lower jaw to a closed position adjacent to said lower jaw, and when said upper jaw is in said closed position, said grasping protrusion surface is embedded in and contacts said groove;
    wherein when said needle is positioned between said lower and upper jaws in the open position, and said upper jaw is moved to the closed position, said needle is grasped between said grasping protrusion surface and said lower jaw ledge surfaces; and
    wherein when said suture filament is positioned between said lower and said upper jaws in the open position, and said upper jaw is moved to the closed position, said suture filament is secured between said groove and said grasping protrusion surface embedded in said groove.

2. The needle holder of claim 1 wherein said upper jaw has a pair of spaced-apart upper floor surfaces, said grasping protrusion surface is interposed between and extends downwardly from said upper floor surfaces, and when said upper jaw is in said closed position, said pair of upper floor surfaces are adjacent said pair of lower floor surfaces.

3. The needle holder of claim 2 further comprising a handle assembly for moving the upper jaw from the open position to the closed position, and a shaft coupling said lower and upper jaws to said handle assembly.

4. The needle holder of claim 3 wherein said handle assembly has a force limiting coupling therein for limiting the grasping force to said jaws when said upper jaw is moved from its open to closed positions.

5. The needle holder of claim 4 wherein said upper jaw is pivotally attached to said shaft.

6. The needle holder of claim 5 wherein each of said lower jaw ledges has an inner ledge surface extending from said ledge surface to said lower floor surface, said upper jaw has a top surface thereon and a pair of spaced-apart outer jaw surfaces, each of said outer jaw surfaces extending from said top surface to said upper floor surface;
    wherein when said suture filament is secured between said groove and said grasping protrusion surface embedded in said groove, said suture filament is interposed between said inner ledge surfaces of said lower jaw ledges and said outer jaw surfaces of said upper jaw.

* * * * *